United States Patent [19]

Collins, Jr.

[11] Patent Number: 4,608,159

[45] Date of Patent: Aug. 26, 1986

[54] BOILER WATER/BOILER FEED WATER AUTOMATIC SAMPLER SYSTEM

[75] Inventor: Henry R. Collins, Jr., Livingston, Tex.

[73] Assignee: Collins Products Company, Inc., Livingston, Tex.

[21] Appl. No.: 602,818

[22] Filed: Apr. 23, 1984

[51] Int. Cl.⁴ .................................................. C02F 1/02
[52] U.S. Cl. ..................................... 210/101; 210/102; 210/103; 210/149
[58] Field of Search ................. 210/739, 741, 742, 88, 210/89, 98, 101, 102, 103, 143, 149; 55/34, 198

[56] References Cited

U.S. PATENT DOCUMENTS

| | | | |
|---|---|---|---|
| 2,619,327 | 11/1952 | Hillier | 210/101 |
| 2,676,574 | 4/1954 | Wenzel | 210/98 |
| 2,780,357 | 2/1957 | Robinson | 210/101 |
| 3,262,878 | 7/1966 | Beckley et al. | 210/921 |
| 3,291,308 | 12/1966 | Headrick et al. | 210/101 |
| 3,598,238 | 8/1971 | Collins | 210/316 |
| 4,439,325 | 3/1984 | Blais | 210/103 |

OTHER PUBLICATIONS

Industrial Instruments for Measurement and Control by Rhodes, 1st Edition, McGraw Hill Book Co., New York, pp. 186, 187, and 466-470, 1941.

Primary Examiner—John Adee

[57] ABSTRACT

A sampling system for boiler water or boiler feed water has an actuator actuated by an external actuator including the following components. A source to supply water having a prescribed temperature and within a prescribed pressure. A flow regulating means with indicator providing a flow of water to a plurality of samplers. A backpressure means controls pressure of water entering the sampler. A piston and cylinder is used to deliver water to the sample station at a rate prescribed by the external actuator.

10 Claims, 2 Drawing Figures

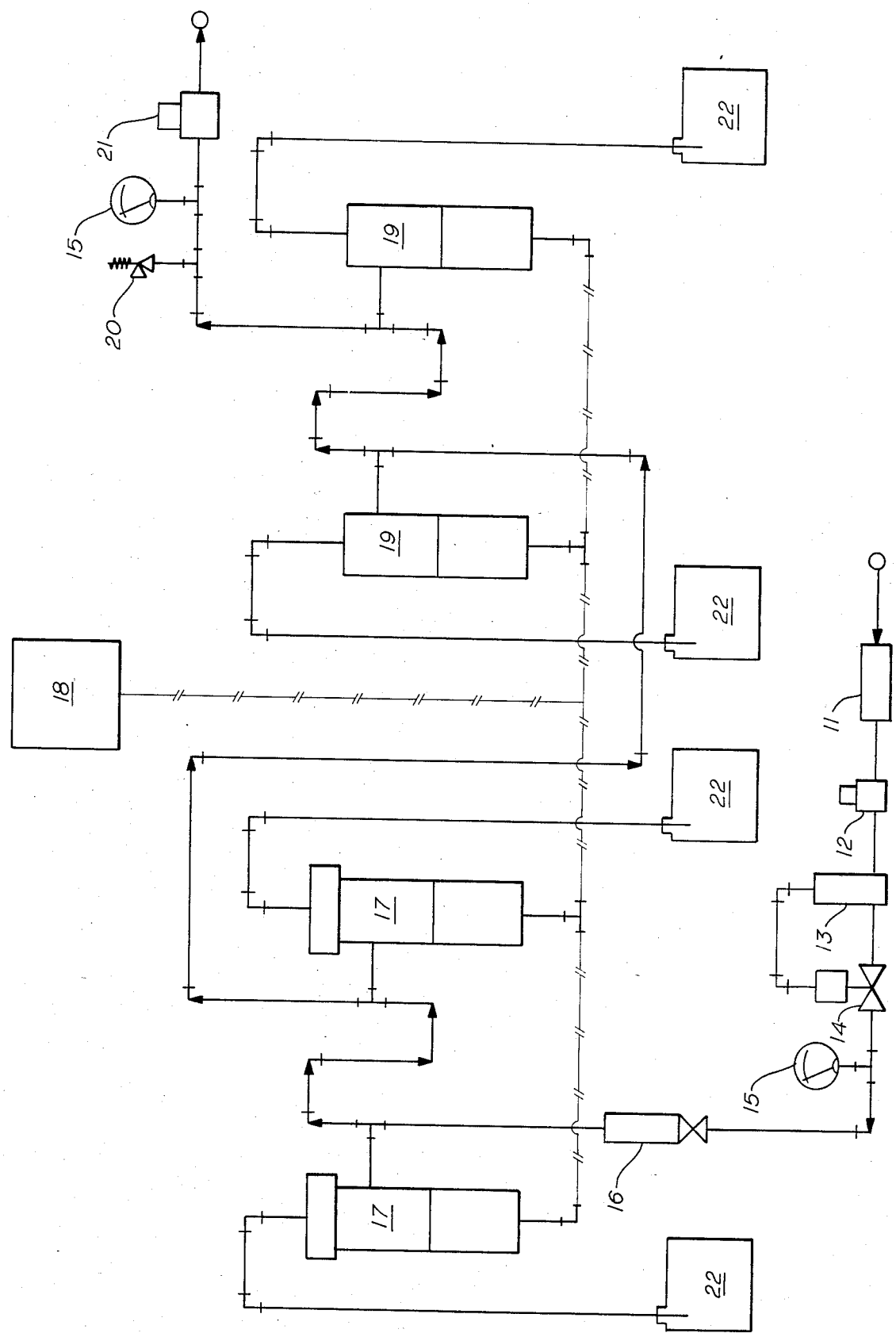

ated water sampling system designed to continuously
BOILER WATER/BOILER FEED WATER AUTOMATIC SAMPLER SYSTEM

BACKGROUND OF THE INVENTION

This invention relates to water sampler systems, and more particularly to an automatic water sampler system connected to piping conduits which transport water to, and from, high pressure, high temperature boiler arrangements.

DESCRIPTION OF THE PRIOR ART

In practically all industrial enterprises wherein high temperature, high pressure boilers are utilized, there arises the need to test the quality and content of water being fed to, and flowing from, such boilers. These tests often reveal the presence of rust or other solids in the water streams, which upon analysis may indicate the necessity for replacing certain pieces of equipment, or for instituting certain quality control procedures to remove such debris either upstream or downstream of the boiler system. Sampling is also used to monitor chemical addition or chemical level in the boiler water to prevent scale deposits and corrosion in equipment.

While many water sampler systems have been revealed in the related prior art, e.g. U.S. Pat. No. 3,598,238 and applicant's continuation-in-part application, Ser. No. 523,876 now U.S. Pat. No. 4,533,471, it is the applicant's belief that none of these systems provide the novel features of construction, arrangement, or combination of parts hereinafter more fully described for the present invention claims hereto appended. The disclosures of said U.S. Pat. No. 4,533,471 and No. 3,598,238 are specifically incorporated herein by reference.

SUMMARY OF THE INVENTION

The present invention details an automatically actuated water sampling system designed to continuously collect composite filtered and unfiltered samples from boiler water/boiler feed water streams. Further, the presently disclosed system regulates pressure and temperature at the sample point, while maintaining a continuous and metered flow of sample water through the sampler system.

For a better understanding of the invention, and to show how it may be carried into effect, the same will now be described by way of example with reference to the accompanying diagrammatic drawings in which:

BRIEF DESCRIPTION OF THE DRAWINGS

FIG. 1 illustrates a schematic diagram of the preferred embodiment of the present invention; and FIG. 2 is a schematic diagram of the units 17 and 19 illustrated in FIG. 1.

DESCRIPTION OF THE PREFERRED EMBODIMENTS

In brief, the sampler system detailed hereinbelow includes a sample cooler, a pressure regulator, a high temperature shut-off valve, a pressure gauge, pressure relief valves, check valves, rotameter, a plurality of samplers, sampler timer electronics, solenoid valves, and air cylinders.

Flow enters the sampler at the entrance of a sample cooler where the water is cooled. A temperature cut-off valve is mounted in the system to control the temperature of water entering the system. Sample pressure is reduced to a preferred range with a pressure regulator. A sampler having a measuring chamber, meters a precise amount of sample into a sample container. A piston, driven by a driver air cylinder, is used to measure the sample taken during each sample cycle. The measuring chamber is bored to accept the piston, which is connected to an air cylinder. Each measuring chamber has two openings or ports disposed in the piston cavity section. An inlet port allows the sample to fill the piston cavity, while an outlet port permits egress of the sample. A check valve is installed at the inlet port, and a pressure relief valve is installed at the outlet port. Air is normally applied to the air cylinder so as to keep the piston extended into the measuring chamber. When taking a sample, the air cylinder withdraws the piston a distance from the chamber. Such withdrawal of the piston permits the free flow of a new sample through a check valve into the chamber inlet port to fill the void created when the piston was withdrawn. A pressure valve at the outlet port is set at a pressure higher than that of the system so as to prevent flow through the valve to the sample container at normal system pressure. Time sequencing permits the complete filling of the measuring chamber before air is again supplied to the cylinder. When air is supplied to the cylinder, the piston is appropriately displaced to permit flow of the sample through the pressure relief valve which is overcome by the pressure increase in the chamber. A check valve prevents backflow through the inlet port.

In the filtered sample measuring chamber, the sample must first pass through a membrane filter element before exiting through the pressure relief valve into the sample container.

The electronics of the sampler drive a three-way solenoid valve which operate the air cylinders of the measuring chamber when a sample is taken. Time-based sampling, or flow-proportional sampling paced by a flowmeter signal, is utilized to control the sampler. With modification, continuous flushing of the measuring chambers may be achieved in the sampler. To accomplish such flushing, a third port is disposed on the opposite side of the measuring chamber from the existing inlet port. Sample flows through the check valve into the piston cavity and out of the third port in the chamber. Flow from the metering chamber immediately enters a solenoid valve. Flow exiting the solenoid valve is required for each chamber outlet port. A stream continuously flows through the chamber and solenoid valve until a sample is obtained. When collecting a sample, the solenoid valve on the chamber outlet port is closed immediately, and air to the air cylinder is turned off. When the measuring chamber is filled with sample, air pressure is again applied to the air cylinder to force the sample through the pressure relief valve. A short time delay is required to hold the valve at the chamber outlet port in its closed position until the sample is forced through the pressure relief valve.

The system described herein may contain a plurality of filtered and/or unfiltered samplers since many applications may require such a configuration.

It is also contemplated that perhaps a heat exchanger may not be of necessity in the sampler cooler to cool the sample as sufficient cooling may be obtained in the tubing between the sample point and sampler. It is also possible that other components of the sampler may not be required in certain applications.

Referring now to FIG. 1, a sample cooler 11 is adapted to cool water entering the sampler to a temperature below 125° F. The cooler contains a 20 foot section of stainless steel tubing with which to carry out its intended purpose. After the sample water has been sufficiently cooled, it is then directed through a pressure regulator 12 having a maximum inlet pressure of 3000 PSI. The regulator 12 reduces the pressure of the incoming sample water to a pressure range of preferably from 5 to 30 PSI. As a precautionary measure, a temperature cut-off actuator 13 is disposed adjacent the outlet of the pressure regulator 12 to ensure maintenance of the sample water temperature below 125° F. If the sample water exiting the pressure regulator 12 is above 125° F., the temperature cut-off actuator 12 will activate its associated solenoid valve 14 to prevent the further ingress of sample water into the sampler. Once an acceptable sample water temperature has been achieved, the solenoid valve 14 will be opened by the temperature cut-off actuator 13 to again allow passage of the stream of sample water;

The sample water stream is then transmitted by conduit through a rotometer flowmeter 16 having a regulating valve to maintain the ingress of sample water into the sampler to 50 cc/minute. Disposed between the temperature cut-off valve 13 (and its associated solenoid valve 14) and the rotameter 16, is a pressure gauge 15 which serves to indicate that sample water entering the rotameter 16 is within the appropriate pressure range. If the pressure gauge 15 indicates that the pressure of the incoming sample water is too high or too low, the pressure regulator 12 may be appropriately reset. Should system pressure exceed 100 psi, a pressure safety valve 20 set at 100 psi will be activated to relieve the excess pressure within the system.

The stream of sample water exiting the rotameter 16 is then transmitted to a plurality of filtered and unfiltered sampler means, 17 and 19, respectively. As detailed in FIG. 1, the regulated stream of sample water is transmitted to the tops of the sampler dispenser means 17 and 19.

As shown in U.S. Pat. No. 3,598,238, each of the sampler means is disposed with a measuring chamber which meters a precise amount of sample water prior to the passage of the samples into sample containers 22. A back pressure valve 21 provides back pressure for the sample water into dispenser means 17 and 19. The measuring chambers of the samplers 17 and 19 are preferably bored to accept a ¾ inch diameter piston and U-shaped cup seals to prevent leakage around the piston. The piston is directly connected to an air cylinder having a 1 inch stroke. Each chamber also details a piston cavity which includes an inlet port and an outlet port. The inlet port, having a check valve installed therein, permits the filling of the piston cavity and the outlet port which includes a pressure relief valve, permit passage of the sample water out of the piston cavity.

In operation, air is supplied to an air cylinder connected to the piston to extend the piston a distance of 1" into the measuring chamber. When a sample is to be taken, the piston is withdrawn from the chamber a distance of 1" by the air cylinder. This withdrawal of the piston permits the ingress of another measured amount of sample water through the check valve into the chamber inlet port to fill the cavity created when the piston was withdrawn.

An air pressure relief valve at the air cylinder of each chamber cavity is set at a higher pressure than that of the system so as to prevent flow through the valve into the sample container at normal system pressure. The system is time-sequenced, and a sufficient amount of time is allotted to allow for the complete filling of the measuring chamber prior to switching the air to the air cylinder. When air is switched in the cylinder, the piston again moves a distance of 1" into the chamber to displace the sample through the pressure relief valve into the sample container 22.

The sampler electronics, indicated at 18, drive a three-way solenoid valve to operate the measuring chamber air cylinders when a sample is taken as is disclosed in applicant's continuation application, Ser. No. 523,876. While time-based sampling has been taught hereinabove, it is conceived herein that flow-proportional sampling, or the like, may be utilized to control the sampler.

FIG. 2 shows an arrangement suitable for use as the sampler means 17 or 19 and wherein flushable filters may be used such as shown in application Ser. No. 523,876.

As shown, filters 10x and 10y are connected to opposite sides of a valve and limited backflushing apparatus 100 which is operated in turn by compressed air supplied by a generator 102 which in turn is controlled by the timing device 18. Such an arrangement is shown and described in greater detail in U.S. Pat. No. 3,598,283 and accordingly will not be described in detail here. The relatively small diameter of the conduits at 105 provides a back pressure effect which eliminates the need for the solenoid valve. When, for example, a piston is pushed into a cavity 100b, a cavity 100a fills with filtered liquid and vice versa. The cavities each hold about 10 cc of fluid. The filtered liquid sample flows through conduits and the apparatus 105 to a respective sampler station or analyzer 22. Backflushing occurs when the timer 18 operates the apparatus 102 and switches air flowing to the air cylinder. The right side piston then moves to displace the liquid in the cavity 100a forcing most of the 10 cc of filtered liquid through 105 and closing off line 110 and filter 10k. This action allows the filter elements to be self-cleaning by dislodging particles on the upstream side of the filter surface as disclosed in Ser. No. 523,876. Filtered liquid now fills the cavity 100b from the back pressure provided by back pressure valve 21a going through apparatus 105 to the analyzers.

It should be noted that about 2 to 6 gallons a minute of liquid flows through line 106 and about 100–200 cc per minute through the filter which is open into the analyzer.

Another embodiment of the present invention (not shown) contemplate the continuous flushing of the measuring chambers as disclosed in applicant's continuation-in-part application, Ser. No. 523,876. In such an embodiment, by-pass outlet port may be disposed on that side of the measuring chamber opposite the existing inlet port. In such an arrangement, sample water flows through the check valve into the piston cavity and out the by-pass port into the chamber. Flow out of the measuring chamber immediately enters a solenoid valve. The solenoid valve outlet may go to drain. In this embodiment, a solenoid valve is required for each chamber outlet. The sample stream continuously flows through the chamber and solenoid valve until a sample is taken. To collect a sample, the solenoid valve on the chamber outlet is immediately closed, and air supplied to the air cylinder is turned off. Once the chamber is filled with sample water, air pressure is again applied to the air cylinder, forcing the sample through the pressure relief valve. A short time delay is herein required to hold the valve on the chamber outlet in its closed position until the sample is forced through the pressure relief valve.

Although the present invention has been described in detail with reference to a preferred form, it will be appreciated that additions, modifications, substitutions, variations and deletions may be undertaken without deporting from the spirit and scope of the invention.

In summary, the objects and advantages of the present invention are attained in a sampling system actuated by an external actuator means 18 for continuously dispensing samples of boiler water or boiler feed water to respective sample stations 22 for analysis, including source means 11–14 supplying the sample water below a prescribed temperature and within a prescribed pressure range such as a pressure indicating and regulating means 12, 15, and excessive temperature flow cutoff means 13, 14. A flow regulating means including flow indicator means 16 provides the sample water at a prescribed flow rate to a plurality of sampler dispensing means 17 and 19. A back pressure regulator means 21 supplies a prescribed back pressure to the sample water which enters into the sample dispensing means 17 and 19 Each of the sampler dispensing means includes a piston and cylinder means 100 which supplies a prescribed volume of sample water to its sample station 22 with each compressive stroke of the piston 100a or 100b into its respective cylinder and driver means 100–102 which successively drive the piston into the cylinder at a rate prescribed by the external actuator 18. The back pressure returns the piston as an intake stroke between each compressive stroke as described. The sampler dispensing means 17 or 19 may include two piston and cylinder means 100a and 100b respectively supplying a prescribed volume of sample water to the sample station and a driver 100 alternately driving each piston successively into its cylinder at a rate prescribed by the external actuator 18. The back pressure will alternately return each piston as an intake stroke between each said compressive stroke.

Each sampler dispensing means may further include a filter means 10x–10y to filter the sample water passing through the piston and cylinder means.

Because many varying and different embodiments may be made within the scope of the disclosed inventive concept, and because modifications may be made in accordance with the descriptive requirements of the law, it should be understood that the details herein are to be interpreted as illustrative, and not as limiting.

What is claimed:

1. In a sampling system actuated by an external actuator means for continuously dispensing samples of boiler water or boiler feed water to respective sample stations for analysis as herein described, the combination comprising:
   (a) source means supplying the sample water below a prescribed temperature and within a prescribed pressure range;
   (b) flow regulating means including flow indicator means for providing the sample water at a prescribed flow rate to a plurality of sampler dispensing means;
   (c) back pressure regulator means for supplying a prescribed back pressure to said sample water which is entering into said sample dispensing means;
   (d) each said sampler dispensing means comprising:
     (1) a piston and cylinder means supplying a prescribed volume of sample water to said sample station with each compressive stroke of the piston into the cylinder;
     (2) driver means successively driving said piston into said cylinder at a rate prescribed by said external actuator; and
     (3) said back pressure returning said piston as an intake stroke between each said compressive stroke.

2. The combination of claim 1 wherein each said sampler dispensing means includes:
   (a) two piston and cylinder means respectively supplying a prescribed volume of sample water to said sample station;
   (b) driver means alternately driving each piston successively into its cylinder at a rate prescribed by said external actuator; and
   (c) said back pressure alternately returning each said piston as an intake stroke between each said compressive stroke.

3. The combination of claim 1 wherein each sampler dispensing means further includes filter means to filter the sample water passing through said piston and cylinder means.

4. The combination of claim 2 wherein each sampler dispensing means further includes filter means respectively connected to one of said piston and cylinder means which is self-cleaning while said piston passes through its compressive stroke.

5. The combination of claim 1 wherein said source means supplies said sample water at a temperature below 125° F.

6. The combination of claim 1 wherein said source means includes cooler means, pressure indicating and regulating means and excessive temperature cut-off means.

7. The combination of claim 1 wherein said flow indicator means is a "Rotometer".

8. In a sampling system actuated by an external actuator means for continuously dispensing samples of boiler water or boiler feed water to respective sample stations for analysis as herein described, the combination comprising:
   (a) source means supplying the sample water below a prescribed temperature and within a prescribed pressure range;
   (b) flow regulating means for providing said sample water at a prescribed flow rate to a plurality of sampler dispensing means;
   (c) back pressure regulator means for supplying a prescribed back pressure to said sample water which is entering into said sample dispensing means;
   (d) each said sampler dispensing means comprising:
     (1) a piston and cylinder means supplying a prescribed volume of sample water to said sample station with each compressive stroke of the piston into the cylinder;
     (2) driver means successively driving said piston into said cylinder at a rate prescribed by said external actuator;
     (3) said back pressure returning said piston as an intake stroke between each said compressive stroke; and (4) filter means for filtering all sample water supplied to said sample station.

9. The combination of claim 8 wherein each said sampler dispensing means includes:
   (a) two piston and cylinder means respectively supplying a prescribed volume of sample water to said sample station;
   (b) driver alternately driving each piston successively into its cylinder at a rate prescribed by said external actuator;
   (c) said back pressure alternately returning each said piston as an intake stroke between each said compressive stroke; and
   (d) filter means for filtering all sample water supplied to said sample station.

10. The combination of claim 9 wherein each sampler dispensing means further includes filter means respectively connected to each of said piston and cylinder means which is self-cleaning while said piston passes through its compressive stroke.

* * * * *

UNITED STATES PATENT AND TRADEMARK OFFICE
CERTIFICATE OF CORRECTION

PATENT NO. : 4,608,159
DATED : August 26, 1986
INVENTOR(S) : Henry R. Collins, Jr.

It is certified that error appears in the above-identified patent and that said Letters Patent is hereby corrected as shown below:

Figure 2 should be added as shown below:

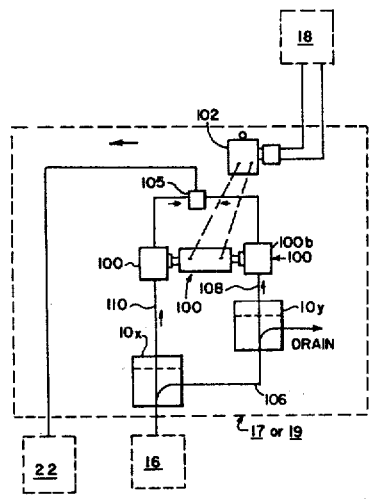

FIG. 2

Signed and Sealed this

Eighteenth Day of November, 1986

*Attest:*

DONALD J. QUIGG

*Attesting Officer*  *Commissioner of Patents and Trademarks*